United States Patent [19]

Mruk et al.

[11] Patent Number: 4,588,762

[45] Date of Patent: May 13, 1986

[54] PRESSURE SENSITIVE ADHESIVE COMPOSITIONS FOR MEDICAL ELECTRODES

[75] Inventors: Norbert J. Mruk, Williamsville; Raymond C. Vaughan, Hamburg; Arthur R. Eddy, Jr., Depew, all of N.Y.

[73] Assignee: Graphic Controls Corporation, Buffalo, N.Y.

[21] Appl. No.: 673,552

[22] Filed: Nov. 20, 1984

Related U.S. Application Data

[63] Continuation-in-part of Ser. No. 555,071, Nov. 25, 1983, Pat. No. 4,559,950.

[51] Int. Cl.$^4$ .................. C07C 143/24; C07C 143/56
[52] U.S. Cl. ........................................ 524/45; 524/272; 524/434; 604/897; 428/355; 428/356; 252/500; 252/510; 252/511; 156/327; 156/328
[58] Field of Search ................ 128/640, 335; 604/897; 524/45, 55, 270, 272, 274, 434; 428/40, 355, 356, 901; 252/500, 510, 511; 156/327, 328

[56] References Cited

U.S. PATENT DOCUMENTS

| | | | |
|---|---|---|---|
| 4,098,945 | 7/1978 | Oehmke | 252/500 |
| 4,147,831 | 4/1979 | Balinth | 428/356 |
| 4,299,231 | 11/1981 | Karmann et al. | 252/500 |
| 4,393,080 | 7/1983 | Pawelchak et al. | 428/356 |

Primary Examiner—John Kight
Assistant Examiner—Nathan M. Nutter
Attorney, Agent, or Firm—M. G. Berkman

[57] ABSTRACT

A heterogeneous, pressure-sensitive, electrically conductive adhesive for disposable biomedical electrodes. The adhesive consists of two phases: a viscoelastic polymeric adhesive phase and an electrically conductive aqueous phase containing a water receptive polymer, a humectant, and an electrolyte. Both phases are intimately interdispersed and the adhesive is applied as a relatively thin film on a supporting substrate. The adhesive is characterized in that it establishes a physical equilibrium with the ambient system so that varying concentrations of moisture in the atmosphere are accommodated and tolerated by the adhesive without loss of viscoelastic and adhesion capabilities and without impairment of electrical conductivity values even under conditions of both high and of low relative humidity.

14 Claims, 2 Drawing Figures

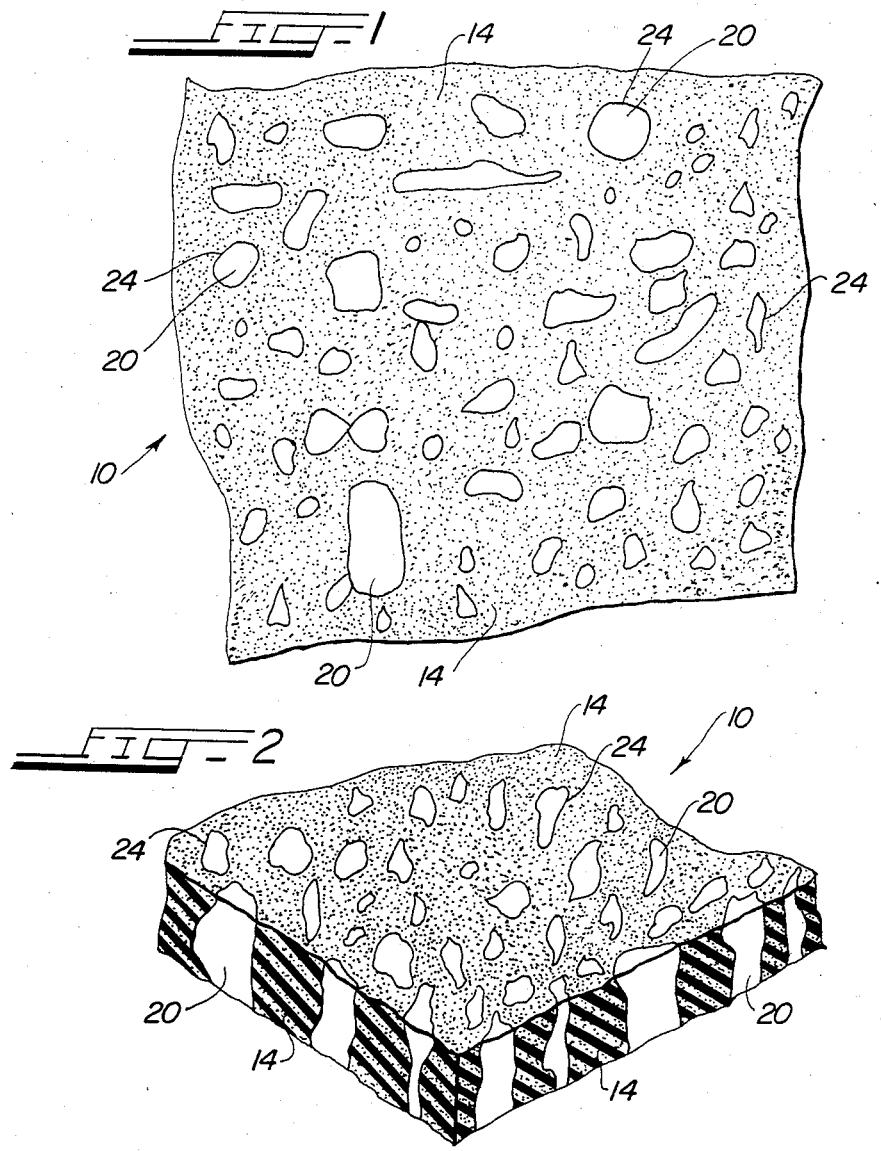

PRESSURE SENSITIVE ADHESIVE COMPOSITIONS FOR MEDICAL ELECTRODES

This application is a continuation-in-part of Vaughan et al. application Ser. No. 06/555,071 filed Nov. 25, 1983 and now U.S. Pat. No. 4,559,950.

BACKGROUND OF THE INVENTION

The present invention relates to adhesives for use in conjunction with disposable biomedical electrodes. More particularly, the invention is directed to biomedical electrode adhesives which are of the pressure sensitive type and which are electrically conductive for establishing an electrical circuit between the skin of a patient and an electro medical device such as an electrocardiograph.

The prior art is replete with various types of biomedical electrodes which vary not only in their mechanical construction but in the use of particular body attachment means as well as electrically conductive circuits including conductive media which constitute part of the electrode assemblies themselves. The general aim of the electrodes, whether used as diagnostic devices or for electro surgery or for stimulation purposes, is to establish good electrical continuity and signal transmission between a patient's skin surface and the electrical leads connected to a specific piece of diagnostic or therapeutic equipment. Among the generally common components of prior art electrodes are structures which include a conductive support element, which may be metallic or which may have been otherwise rendered conductive, to which an electrical lead line or wire from an associated apparatus may be conveniently attached.

Many electrodes rely upon the use of a conductive electrode paste or gel which is applied or otherwise interposed as a conductive medium between the conductive suppport element of the electrode and the skin surface interface. Still other electrodes utilize a sponge or pad which is impregnated with or which contains an electrolyte solution or paste. The goal in each electrode structure is to establish a continuous and reliable contact and circuit between the skin surface of the patient and the electrical leads to the apparatus being used. Electrical artifacts are to be avoided, as are "hotspots" or localized zones of high current concentration and transmission.

Many of the prior art publications, including prior patents, are directed to particular formulations of conductive gels or pastes of the type used in conjuncton with disposable biomedical electrodes. While in a preferred embodiment of the present invention conductive gels are used to augment and enhance the corductive characteristics of the assembly and to ensure continuous contact between the conductive element of the electrode and the body skin surface, the present invention is not directed to the conductive paste or gel itself. Many gel formulations are suitable in the practice of the present invention. Such conductive gels are described in Vaughan, et al. patent application Ser. No. 555,071 entitled "Disposable Bio-Medical and Diagnostic Electrode", filed Nov. 25, 1983. The entire disclosure of that application is hereby specifically incorporated herein by reference to the extent that it is not inconsistent herewith.

The present invention is directed not to the conductive gel or to any specific "mechanical" feature of the disposable biomedical electrode but, rather, to an improved electrode conductive adhesive by means of which the electrode is secured to and retained in electrical communication with the skin of the patient.

In order to ensure a meaningful understanding of the present invention, and to enable classification of the invention in the appropriate, precise art that is relevant, certain facts pertaining to pressure-sensitive adhesives and to gels, conductive pastes, and adhesives in general are set forth herebelow. The pressure-sensitive adhesives of the present invention, as applied to biomedical electrodes can be considered to constitute modified forms of adhesives of the type used on adhesive tapes, the general purpose of which is to secure the tape backing onto the surface to which it is applied. In the present application, the function of the adhesive is not only to secure the electrode backing firmly to the patient's skin but also to provide a current path between the electrode itself and the skin surface.

In general, adhesive tapes may be divided into three principal classes depending upon the manner in which the adhesive itself is activated, whether by means of solvent, heat, or the application of finger pressure. Solvent activated tapes or "gummed tapes" are usually activated by applying water to the tape surface, the water serving as a solvent. Typical examples include tapes used for sealing cartons, envelope flaps and postage stamps. In some relatively rare industrial applications, non-aqueous solvents are used to activate the "dry" solvent-activated compositions. In all of the solvent-activated-type tapes, the adhesion increases and a bond forms as the solvent evaporates. Generally, the substrates are marred or destroyed when the tape is ultimately removed.

In adhesives of heat-activated tape, the combination of heat and pressure applied makes the adhesive sticky. Tapes such as used in garment repair or fabric mending, or for the application of "patches" on clothes are typical examples of heat-activated tapes. In this system, the adhesive bond is produced as a result of penetration and cooling, and is normally strong. The adhesion or bond is "irreversible".

Tapes in which the adhesive is activated by applying finger pressure are referred to as "pressure-sensitive tape". The adhesive itself is referred to as a pressure-sensitive adhesive (PSA). A pressure-sensitive adhesive has been defined as viscoelastic material which in solvent-free form remains permanently tacky.

These adhesives adhere instantaneously to most solid surfaces upon application of only relatively light finger pressure. PSA tapes can usually be removed cleanly from the surfaces to which they have been applied. In general, their adhesive strength is of a lower order of magnitude than that exhibited by solvent or by heat-activated tape adhesives. Typical examples of PSA tapes and adhesives are "Scotch" ® tape, masking tape, medical adhesive tape, Band-aids ®, Curad ® tapes and disposable ECG electrodes.

Many different formulations of pressure-sensitive adhesives have been used for many purposes. However, such formulations ordinarily include components which find their counterpart from formulation to formulation. Such ingredients are elastomers, tackifiers, plasticizers, fillers, and antioxidants. The performance characteristics of a pressure-sensitive adhesive are dependent primarily upon three properties: tack, adhesive strength, and cohesive strength. In the manufacturing process, PSA's are ordinarily coated onto release liners or substrates at a stage in which the adhesive is either a solvent phase or an aqueous latex, or a hot melt composition. In the first two examples, the adhesive is dried by application of heat to dispel the solvent or the water present in the coated formulation. In contrast, the hot melt compositions require only that they be permitted to cool to become solid, thereby to establish the requisite tack properties. Pressure sensitive adhesive compositions are ordinarily protected by the release liner during storage and prior to their use, for example, the plastic backing on a product such as Band-aids ® and Curads ®. In roll form, the adhesive tape's upper surface serves as its own release liner.

It will be appreciated that neither electrode gels nor pastes come within the definition of pressure-sensitive adhesives. These products (gels and pastes) differ from each other in that the paste normally contains mineral fillers and a lower concentration of water. The ingredients present provide the paste with an opacity, a higher viscosity, and usually a greater degree of tackiness in its wet condition. While there are certain areas in which some similarity exists between electrode gels and pastes, on the one hand, and electrically conductive pressure sensitive adhesives, on the other hand, such areas are primarily in their functional capabilities. Both types of materials serve as conductive media for medical electrodes. The pressure-sensitive adhesives of the present invention serve the additional function of securing the electrode base in a close and contiguous bonded relationship with the patient's skin. Furthermore, the conductive adhesives of the present invention exhibit cohesive strength and non-drying properties allowing the adhesive coated electrode to be removed cleanly from the skin without leaving any substantial residue.

Electrically conductive pressure sensitive adhesives for use in conjunction with medical electrodes are known in the prior art. Some of these preparations utilize gums such as karaya gums which produce what may be described as homogeneous adhesives based on water soluble gelling agents. Such systems have the disadvantage of not being sufficiently compatible with electrolytes such as sodium chloride and potassium chloride. The omission of such salts from the electrolyte system impairs the utility of the final product and impairs the ability of the electrodes to be defibrillated in use. The karaya gum-type adhesives are also objectionable in that the compositions must be poured into molds and heated to produce the gelled product. Such gum systems do not tolerate significant concentrations of electrolytes.

Another class of prior art conductive pressure-sensitive adhesives used in conjunction with medical electrodes involves polymeric homogeneous systems. The polymers used in such systems are water soluble or at least strongly hydrophilic in nature. The published literature disparages applicants' type of heterogeneous system and actually "teaches away" from such a system.

Others of the prior art conductive pressure-sensitive adhesives lack specific ingredients which are believed to be necessary to enhance and maximize the efficacy of the adhesive. For example, such prior art preparations fail to include a humectant, or a humectant in a concentration sufficient to maintain and ensure conductivity within a broad range of relative ambient humidity. Such prior art preparations tend to dry-out under many ambient conditions and thereupon lose electrical conductivity.

It is, therefore, a principal aim of the present invention to provide an improved electrically conductive pressure-sensitive adhesive for use with disposable biomedical electrodes, such adhesives exhibiting markedly enhanced stability and adhesive properties and avoiding many of the shortcomings of prior art preparations.

SUMMARY OF THE INVENTION

The pressure-sensitive adhesive of the present invention is a stable, heterogeneous network of a polymeric viscoelastic phase and electrically conductive aqueous zones. The combination and intercooperation of these two distinct phases results in a conductive pressure-sensitive adhesive characterized by both useful adhesive properties and highly effective and stable electrical conductivity properties. While there have been prior attempts to achieve a stable heterogenous network, such attempts have met with only limited success.

In accordance with the practice of the present invention the improved adhesives are related to the use of aqueous compositions of water soluble or water swellable polymers, in combination with an electrolyte and a humectant. In the system described, such polymers stabilize the zones in the aqueous network without destroying the tack, adhesive or cohesive properties of the viscoelastic polymer phase.

It is an additional important feature of the present invention that the aqueous composition contains a sufficient concentration of a humectant to retain moisture and ensure conductivity within a broad range of relative humidity ambient conditions. The stabilization of the conductive aqueous network is evidenced by the retention of unimpaired electrical conductivity, by the pressure-sensitive adhesive properties exhibited, and by the imparting of a dry "feel" across a broad range of relative humidity conditions.

In accordance with the present invention, the elimination or absence of any one of the critical ingredients of the aqueous composition described above produces a pressure-sensitive adhesive without the useful and functional properties which characterize the present invention. For example, if the water soluble or swellable polymers are not present, then there results a pressure-sensitive adhesive which lacks cohesive strength and which feels very wet when exposed to high relative humidity. The sensed wetness is due to a film of surface moisture. This same aqueous film is responsible for a serious loss of the adhesive properties. The presence of the water soluble or swellable polymers in the pressure-sensitive adhesive formulation of the invention reduces any tendency for this "wetting" of the surface to occur and improves the adhesion, the cohesion and the resistance of the product to the adverse effect of relatively high humidity.

If a high concentration of humectant is not present in the formulation of the invention, the aqueous phase will tend to dry and a very high electrode impedance will result. Finally, if the electrolyte is not maintained above a prescribed minimum concentration, the pressure-sensitive adhesive will retain moisture but will exhibit an unsatisfactorily high electrode impedance.

Many of the important advantages and desirable features of the pressure-sensitive adhesives of the invention are believed to derive from the unique intercooperation of the various components which constitute the composition itself. In addition, it has been found that the prepared compositions exhibit remarkable flexibility and ease of coating. These practical attributes appear to be inherent in the aqueous latex pressure-sensitive adhesives as formulated. For example, the adhesives of the invention may be conveniently coated upon almost any substrate or surface in essentially the same manner as are other latex preparations. When conventional coating techniques and drying procedures are used in the practice of the present invention, there is produced a relatively thin layer (for example 2.5 mils) of a conductive adhesive film.

An important advantage of the present invention over prior art products and techniques is the ease of coating and converting. Whereas the prior art preparations and techniques involve depositing a thick layer of hot viscous material and then allowing it to cool and solidify (e.g., karaya gum compositions), or depositing thick viscous layers of synthetic polymer solutions which must then be cross-linked to provide a gel-like state (cross-linking being achieved either catalytically or through chemical means or by irradiation), none of these objectionable techniques is involved in coating the compositions of the present invention.

A significant economic advantage of the present invention is that relatively thin adhesive layers may be used, with corresponding savings in the cost of raw materials. Still other advantages of the compositions and coatings of the present invention are enhanced conductivity and accelerated equilibration to ambient relative humidity. Each of these advantages is believed to stem directly from the reduced thickness of the adhesive film considered in conjunction with the high concentration of humectant.

Adhesive films in accordance with the present invention also exhibit enhanced tack and adhesive properties as compared with prior art conductive pressure-sensitive adhesives.

Yet another important advantageous feature of the product of the present invention is that these compositions permit one to utilize those types of viscoelastic polymers which are possessed of superior adhesive qualities, in combination with electrolyte salts such as sodium or potassium chloride, or ammonium chloride, which produce excellent conductivity characteristics. In contrast, many of the gelling-type polymers used in prior art homogeneous single phase systems (e.g., karaya gum or water soluble polymer based adhesives) suffer from significant incompatability with inorganic salts, thus being restricted in formulation versatility.

Other and further features and advantages of the pressure-sensitive adhesive of the present invention will be evident from a reading of the following specification taken in conjunction with the drawing.

BRIEF DESCRIPTION OF THE DRAWINGS

FIG. 1 is an enlarged schematic representation, as seen through a microscope, of the conductive adhesive film of the invention depicting its heterogeneous composition and showing the latex emulsion derived matrix and, distributed therethrough, the aqueous island-like zones defined by the water-receptive polymer, the aqueous zones extending through the thickness dimension of the film; and FIG. 2 shows a perspective view of the conductive pressure-sensitive adhesive film of FIG. 1.

DESCRIPTION OF PREFERRED EMBODIMENTS

The aims and objects of the invention are achieved by providing in a pressure-sensitive conductive adhesive for application to biomedical electrodes, a two-phase, heterogeneous composition including a viscoelastic polymeric adhesive phase and an electrically conductive aqueous phase. After the pressure-sensitive adhesive has been coated and dried and is ready for use, the aqueous phase is arranged as a series of discrete zones intimately dispersed throughout the continuous phase of viscoelastic polymer. The aqueous phase includes as essential components a water receptive polymer, a humectant, and an electrolyte. The continuous phase of viscoelectric polymer is insoluble or substantially insoluble in water.

Before it is coated onto a substrate, the preferred wet adhesive formulation can be described as a water-based mixture in which the emulsion particles of the viscoelastic polymer are dispersed. Both the humectant and the electrolyte are dissolved in the continuous aqueous phase. The water receptive polymer may be either dissolved or dispersed in the aqueous phase of the wet formulation. This adhesive composition is applied as a relatively thin film or coating on a supporting substrate. Drying of the film or coating drives off enough water to allow the latex particles of viscoelastic polymer to coalesce into a continuous phase, but the humectant prevents total removal of the water and in fact causes water to be reabsorbed from the atmosphere after the drying process is completed. The reabsorbed water is excluded from the continuous viscoelastic polymer phase but is retained along with the humectant, electrolyte, and water receptive polymer in the discrete zones of the aqueous phase.

In this manner the unique balance of components contained in the final adhesive coating or film establishes a physical equilibrium with the ambient system so that varying concentrations of moisture in the atmosphere are accommodated without resulting in any deleterious effects on the adhesive or on the adhesive bond itself. Moreover, such broad variations in the moisture contained in the ambient atmosphere are successfully tolerated by the adhesive without any substantial loss of the viscoelastic and the adhesion capabilities and without loss of electrical conductivity values even under a broad range of high and low relative humidity.

The heterogeneous composition which constitutes the pressure sensitive adhesive of the invention is, in its "dry" utilitarian form, a complex combination of intercooperating component elements. Some of these components are essential to the present invention; others are not. Each component fulfills a useful role. In the following paragraphs, each component is identified and characterized in turn, and the role and function of each are explained.

Principal components of preferred adhesive formulations of the present invention are identified in TABLE I. The table also gives the concentrational

TABLE 1

| Component | Concentrational Range | Preferred Conc. (% by weight) |
|---|---|---|
| Water | 30–60 | 40–50 |
| Latex emulsion (@ 50% viscoelastic polymer solids) | 5–35 polymer solids in wet formulation | 10–20 polymer solids in wet formulation |
| Humectant (e.g. Glycerol) | 10–25 | 15–20 |
| Tackifier (self-emulsifiable hydrocarbon rosin) | 5–25 | 10–20 |
| Electrolyte (Inorganic or | >0–10 | 1–6 |

TABLE 1-continued

| Component | Concentrational Range | Preferred Conc. (% by weight) |
|---|---|---|
| organic salt) | | |
| Water Receptive polymer (e.g. CMC) | 0.2–10 | 0.5–5 |
| Film forming enhancer (polyvinyl alcohol) | 0.5–3 | 0.5–1.5 |
| Cross-linking agent (Zinc acetate Dihydrate, to cross link the latex) | 0.2–1 | 0.25–0.75 | range for each ingredient, as well as the preferred concentrations.

A series of specific formulations is set forth in TABLE II. Products referred to by trade names are identified as to source.

As shown schematically in FIGS. 1 and 2, the conductive adhesive film 10 of the invention is a heterogeneous structure comprising a viscoelastic polymer matrix 14 formed from a latex emulsion and preferably including a tackifier to enhance the adhesive properties. Distributed throughout the matrix 14 are aqueous zones 20 defined and delineated by the bounding water-receptive polymer 24. The aqueous zones contain the water-soluble components of the film, including the electrolyte salt and the humectant as solutes in the aqueous phase delineated by the polymer 24.

Water is the formulating medium. Additionally, it is a component of the latex and the latex-type emulsions used, and of the tackifier. In general, the water concentration is in the range of from about 30 to about 60% by weight, with a concentration of 40 to 50% being preferred. While in the preparation of the preferred embodiments of the invention deionized water or distilled water is preferred, "tap" water is suitable.

TABLE II provided herewith and constituting a part of the present disclosure provides for each of a series of 20 different formulations an identification of the

TABLE II

Conductive Adhesive Formulations (PARTS PER HUNDRED)

| | 1 | 2 | 3 | 4 | 5 | 6 | 7 | 8 | 9 | 10 |
|---|---|---|---|---|---|---|---|---|---|---|
| Deionized Water | 39.0 | 40.0 | 7.0 | 39.0 | 38.0 | 6.0 | 29.0 | 40.0 | 40.0 | 37.0 |
| UCAR 174 (1) | 24.0 | | | | 23.0 | | 25.0 | 24.0 | 24.0 | 24.0 |
| UCAR 175 (1) | | 24.0 | | | | | | | | |
| Flexbond 150 (2) | | | 66.0 | | | | | | | |
| Adcote 73A212 (3) | | | | 25.0 | | | | | | |
| Hartex 103 (4) | | | | | 6.0 | | | | | |
| Hycar 26146 (5) | | | | | | 72.0 | | | | |
| Glycerol | 18.0 | 17.0 | 21.0 | 17.0 | 16.0 | 18.0 | 17.0 | 17.0 | 17.0 | 17.0 |
| Aquatac 9027 (6) | 13.5 | 13.5 | | 13.5 | 13.0 | | | 13.5 | 13.5 | 13.5 |
| Zonester 65 (7) | | | | | | | 24.0 | | | |
| Sodium Chloride | 2.0 | 2.0 | 2.5 | 2.0 | 2.0 | 2.0 | 2.0 | | | |
| Potassium Chloride | | | | | | | | 2.5 | | |
| Ammonium Chloride | | | | | | | | | 1.7 | |
| Potassium Citrate-H2O | | | | | | | | | | 5.1 |
| PVA Vinol 540 (2) | 1.0 | 1.0 | | 1.0 | 0.9 | | 1.0 | 1.0 | 1.0 | |
| Waterlock J-500 (8) | | | | | | | | | | |
| Sodium CMC 7H3SF (9) | | | | | | | | | | |
| Hydroxyethyl Cellulose (1) QP 30000/H | | 2.0 | | 2.0 | | | | | | |
| Ac-Di-Sol (10) | 2.0 | 2.0 | 3.5 | 2.0 | 1.76 | 2.0 | 2.0 | 2.0 | 2.0 | 2.0 |
| Buckeye CLD-2 (11) | | | | | | | | | | |
| Explotab (12) | | | | | | | | | | |
| Waterlock A-100 (8) | | | | | | | | | | |
| Karaya Gum | | | | | | | | | | |
| Sephadex G-200 (13) | | | | | | | | | | |
| Cyanamer (14) P-250 | | | | | | | | | | |
| Zn Acetate Dihydrate | 0.5 | 0.5 | | 0.5 | | | | 0.5 | 0.5 | 0.5 |

| | 11 | 12 | 13 | 14 | 15 | 16 | 17 | 18 | 19 | 20 |
|---|---|---|---|---|---|---|---|---|---|---|
| Deionized Water | 40.0 | 40.0 | 41.0 | 41.0 | 40.5 | 40.0 | 39.0 | 40.0 | 41.0 | 40.0 |
| UCAR 174 (1) | 24.0 | 24.0 | 24.0 | 24.0 | 25.0 | 24.0 | 24.0 | 24.0 | 24.0 | 24.0 |
| UCAR 175 (1) | | | | | | | | | | |
| Flexbond 150 (2) | | | | | | | | | | |
| Adcote 73A212 (3) | | | | | | | | | | |
| Hartex 103 (4) | | | | | | | | | | |
| Hycar 26146 (5) | | | | | | | | | | |
| Glycerol | 17.0 | 17.0 | 17.0 | 18.0 | 17.0 | 17.0 | 16.0 | 17.0 | 18.0 | 17.0 |
| Aquatac 9027 (6) | 13.5 | 13.5 | 13.5 | 13.5 | 13.5 | 13.5 | 13.5 | 13.5 | 13.5 | 13.5 |
| Zonester 65 (7) | | | | | | | | | | |
| Sodium Chloride | 2.0 | 2.0 | 2.0 | 2.0 | 2.0 | 2.0 | 2.0 | 2.0 | 2.0 | 2.0 |
| Potassium Chloride | | | | | | | | | | |
| Ammonium Chloride | | | | | | | | | | |
| Potassium Citrate-H2O | | | | | | | | | | |
| PVA Vinol 540 (2) | | 1.0 | | | | 1.0 | 1.0 | 1.0 | | 1.0 |
| Waterlock J-500 (8) | | 1.9 | | | | | | | | |
| Sodium CMC 7H3SF (9) | | | 1.0 | | | | | | | |
| Hydroxyethyl Cellulose (1) QP 30000/H | | | | 1.0 | | | | | | |
| Ac-Di-Sol (10) | | | | | 2.0 | | | | | |
| Buckeye CLD-2 (11) | | | | | | 2.0 | | | | |
| Explotab (12) | | | | | | | | 3.7 | | |
| Waterlock A-100 (8) | | | | | | | | | 1.7 | |
| Karaya Gum | | | | | | | | | | 1.3 |

TABLE II-continued
Conductive Adhesive Formulations
(PARTS PER HUNDRED)

| | | | | | | | | | | |
|---|---|---|---|---|---|---|---|---|---|---|
| Sephadex G-200 (13) | | | | | | | | | | 2.0 |
| Cyanamer (14) P-250 | 1.9 | | | | | | | | | |
| Zn Acetate Dihydrate | 0.5 | 0.5 | 0.5 | 0.5 | 0.5 | 0.5 | 0.5 | 0.5 | 0.5 | 0.5 |

TABLE II FOOTNOTES
(1) Union Carbide Corp., Danbury, Connecticut
(2) Air Products and Chemicals, Inc., Allentown, Pennsylvania
(3) Morton Chemical Co., Chicago, Illinois
(4) Firestone Natural Rubber and Latex Co., Akron, Ohio
(5) B. F. Goodrich Co., Cleveland, Ohio
(6) Sylvachem Corp., Panama City, Florida
(7) Arizona Chemical Co., Wayne, New Jersey
(8) Grain Processing Corp., Muscatine, Iowa
(9) Hercules Incorporated, Wilmington, Delaware
(10) FMC Corp., Philadelphia, Pennsylvania
(11) Buckeye Cellulose Corp., Memphis, Tennessee
(12) Edward Mendell Co., Carmel, New York
(13) Pharmacia Fine Chemicals AB, Uppsala, Sweden
(14) American Cyanamid Co., Wayne, New Jersey In accordance with the practice of the invention, latex and latex-type emulsions are relied upon as the principal agent for imparting adhesive qualities to the final "dry" pressure sensitive adhesive. As indicated in TABLE II, examples 1 through 6 suggest the scope of the various types of latex emulsions which may be used in the conductive adhesive formulations. Examples 1, 2, 4 and 6 typify the polyacrylate-type polymer, while example 3 illustrates the use of a polyvinyl acetate copolymer latex. Example 5 uses a polyacrylate latex modified with a natural rubber latex (Hartex 103). It is thus readily evident that it is both feasible and practical to blend various latex-type formulations as an alternative to using a single component emulsion composition. In the specific examples illustrated, essentially each latex contains approximately 50% polymer solids. The resulting concentration of latex polymer solids in the overall final wet formulation is between 5% and 35% by weight, with a weight percentage of 10% to 20% being preferred. In addition to the latex products specifically identified, any latex emulsion which is compatible with the other component ingredients and which provides sufficient adhesive strength is suitable.

As previously pointed out, a humectant is used as means for retaining sufficient water within the aqueous phase of the "dry" conductive adhesive to keep the electrolyte salts dissolved, thus to maintain the necessary electrical conductivity characteristics and related properties. The formulations provided are generally structured so as to provide an optimum balance of adhesive and conductive properties at equilibrium with an ambient relative humidity of about 40%. The systems described function dynamically to adjust to changes in relative humidity as such changes occur. Ranges of relative humidity above 40% result in greater electrical conductivity, whereas the reverse is true when the adhesive compositions are exposed to relative humidities below the 40% level. Although glycerol is the specific example identified, and is a preferred humectant, it is contemplated that other polyhydric alcohols may be substituted. Examples of such materials are 1, 2-propylene glycol, ethylene glycol, butylene glycol, sorbitol, sorbitan esters, etc. The concentration range of glycerol in the wet formulation is from about 10% to about 25% by weight, with 15% to 20% by weight being preferred.

Most of the formulation examples shown in TABLE II contain what is characterized as a "tackifier". The function of this component is to increase the adhesive tack properties of the final conductive adhesive. As a general class, the tackifiers found particularly suitable for the purposes of the invention are self emulsifiable hydrocarbon rosins. In all examples except for 3, 6 and 7, the material used is Aquatac 9027, a product of Sylvachem Corp. In example 7, Zonester 65 tackifier, a product of Arizona Chemical Co. is used. Other suitable compositions may be substituted. Examples 3 and 6 indicate that the functional conductive adhesives of the invention can be prepared without the inclusion of a tackifier, although the use of such agents is preferred. In general, the tackifier concentration is in the range from about 10% to about 20% by weight.

Referring now to the electrolyte component, it is evident in TABLE II that sodium chloride is a preferred salt, and constitutes a component in all examples except for 8, 9 and 10. The function of the electrolyte salt is to impart electrical conductivity to the conductive adhesive. Many different types of salts, including both inorganic and organic salts may be utilized. Examples 8 and 9 illustrate the use of potassium chloride and ammonium chloride respectively. Potassium citrate is used in example 10. Substantially any salt may be used provided it posesses the proper solubility and compatibility characteristics for the given formulation, and poses no health hazards. Included among the useful organic salts are the alkali metal citrates, acetates and benzoates. It is contemplated that cationic and anionic organic salts as well as polymers containing cationic or anionic salt groupings would find utility in the practice of the invention. The electrolyte concentration range is from very low concentrations up to a maximum of about 10% by weight in the wet formulation. The preferred concentrational range for alkali metal chloride salts is from about 1% to about 6% by weight.

An essential component of the conductive adhesives of the invention is what may be characterized as a water receptive polymer. The function of these materials is to provide highly viscous "aqueous" zones or areas in the adhesive film. Such electrically conductive zones or "windows" are indicated schematically in FIG 1. Typical polymers of the type found to be useful in the practice of the invention are carboxymethylcellulose and related compounds. Some of these are water soluble while others are water swellable. Water receptive polymers which are cross linked to define wetted gel particles are preferred because the aqueous cells in such structures are sharply defined and will swell or contract as a function of relative humidity. Examples 11 through 20 of TABLE II illustrate the broad range of such water receptive polymers which have been found useful in preparing the conductive adhesives of the invention. The product Ac-Di-Sol (FMC Corp.) is an example of a cross linked carboxymethylcellulose (examples 1 through 10).

In preferred formulations, polyvinyl alcohol is useful in combination with the water receptive polymers to improve the film forming characteristics which are desirable in the system described. Consistent with this fact, the TABLE II includes formulations in which polyvinyl alcohol is a component ingredient.

The concentrational range of the water receptive polymers is determined primarily by their specific effects upon the viscosity and the electrical conductivity. However, generally, the useful concentrational range is between about 0.2% and 10% by weight.

The various types or classes of water receptive polymers, identified in TABLE II, and found to be useful in the practice of the invention are the following:
1. Synthetic polymers:
Example 11 of Table II, Cyanamer (polyacrylamide), a product of American Cyanamid Co.
Example 12, Water Lock J-500 (synthetic polyacrylate) product of Grain Processing Corp.
2. Natural polymers:
Example 19, Karaya gum,
Example 20, Sephadex (cross linked dextran), a product of Pharmacla Fine Chemicals, AB, Uppsala, Sweden.
3. Synthetically modified cellulose polymers:
Example 13, sodium carboxymethylcellulose.
Example 14, hydroxy ethyl cellulose,
Example 15, Ac-Di-Sol (cross linked sodium carboxymethylcellulose) a product of FMC Corp.
Example 16, Buckeye CLD-2 (cross linked sodium carboxymethylcellulose), a product of Buckeye Cellulose Corp.
4. Synthetically modified starch polymers:
Example 17, Explotab (sodium starch glycolate), product of Edward Mendell Co.
Example 18, Water Lock A-100 (starch graft copolymer of polyacrylic acid and polyacrylamide), a product of Grain Processing Corp.

Preferred formulations in accordance with the practice of the invention include a cross linking agent for the purpose of improving the cohesiveness of the conductive adhesive film. In the specific examples provided in TABLE II, the preferred cross linking agent is zinc acetate dihydrate. This chemical functions as a cross linking agent for the UCAR 174 (Union Carbide Corp.) latex. Other cross linking agents may be used, each fulfilling a similar function with respect to the particular latex with which it is combined.

The biomedical electrodes prepared using the conductive adhesive of the present invention find many and varied uses. Typical examples of the products involved are disposable ECG electrodes, electro surgical dispersive (ESD) electrodes, and transcutaneous electrical nerve stimulation (TENS) electrodes. Additionally, the adhesive itself is generally useful in any biomedical procedure requiring an electrically conductive interface between the transducer surface and the skin.

In the case of ECG electrodes, the conductive adhesive is applied as a coating onto a release liner paper (wet thickness of 8 mils, dry thickness of 2.5 mils) and then transferred to a polyester film, the film having been previously coated with a layer of silver/silver chloride.

The utility and efficacy of the resulting assembly were established by conducting tests upon pairs of these silver/silver chloride/polyester film samples attached together face-to-face (0.3 square inch area). The electrical tests were performed according to the Association for the Advancement of Medical Instrumentation (AAMI) Proposed Standard for Pre-gelled ECG Disposable Electrodes. Typical electrical test results obtained were the following:

| | |
|---|---|
| D.C. Offset Voltage | Approximately 1 mV or less |
| A.C. Impedance | 200–800 ohms. |
| Defibrillation Overload Recovery | Passes test. |

Adhesive tests were also performed on samples of the silver/silver chloride/polyester films coated with conductive adhesive. The adhesive tests were performed according to the procedures of the Pressure Sensitive Tape Council (PSTC) directives for the testing of adhesive tapes. Typical adhesive test results were as follows:

| | |
|---|---|
| Rolling Ball Tack (PSTC-6) | 1–2 inches |
| 180 Degree Peel Adhesion (PSTC-1 stainless steel) | Approximately 0.5 lbs./inch. |

In the investigative work and development using the pressure sensitive adhesive of the present invention, it was established from the AAMI electrical results that the products in which the conductive adhesive of the invention is used perform at least as well as those in which a conductive gel in a pre-gelled disposable electrode is used, and that the adhesion strength is clearly sufficient to permit the required adherence to the skin surface. Additionally, it has been established that the conductive adhesive possesses sufficient cohesive strength to permit easy removal from the skin without leaving any substantial undesirable residue. Prototype ECG electrodes constructed using samples of the conductive-adhesive-coated silver/silver chloride/polyester films were successfully tested on human volunteers and were shown to exhibit stable ECG traces of normal amplitude and resolution.

In still another series of tests establishing the broad efficacy of the conductive adhesives of the invention, two aluminum plates (approximately 20 square inches) were coated with the electrically conductive adhesive in the same manner as applied in the case of the ECG electrodes. The aluminum electrodes were then attached to the upper thighs of a human subject, and it was found that excellent adhesive properties were achieved. The thus attached electrodes were then connected to an electro surgical generator so that one electrode functioned as the "active electrode", while the other functioned as the "passive electrode". High frequency current of the conventional type utilized with such equipment, when passed through the pair of electrodes, produced no abnormal heat sensations, showing that the conductive adhesive is clearly capable of functioning as a low impedance interface material on an electro surgical dispersive electrode. The experiments and examples previously described also indicate conclusively that the conductive adhesive of the invention is useful as an electrically conductive interface material for biomedical electrodes used in TENS applications, electromyography, and skin or body impedance measurements.

PREFERRED METHOD OF PREPARING ADHESIVE FORMULATIONS

The general method by which the various components are combined to produce the adhesive of the invention is first to combine, in water, the humectant, the electrolyte salt, the water receptive polymer, and the polyvinyl alcohol to provide a dispersion. The emulsifiable tackifier is then added, and then the latex emulsion followed by the cross linking agent. By way of illustrative example, and not in any limiting sense, a detailed procedure is set forth below:

Method of Formulating Conductive Adhesive Composition

The general method for formulating the conductive adhesives of the invention having been described, the following is provided as a detailed account of the actual preparation of a preferred embodiment, including the quantitative designation of components, and identification, as well, of the particular materials used. The designation of amounts is in parts by weight.

Vinol 540 (Air Products and Chemicals, Inc.) polyvinyl alcohol (0.98 part) and a solution of 2.0 parts of sodium chloride in 18.1 parts of water were added, step-wise, with stirring, to 17.7 parts of glycerol. The resulting mixture was then heated with stirring at 90-100 degrees C. for thirty minutes to dissolve the polyvinyl alcohol. Ac-Di-Sol, (FMC Corp.) cross linked carboxymethylcellulose (2.0 parts) was added at approximately 70 degrees C. while the solution was being cooled to room temperature. The resulting dispersion constitutes mixture A.

In a separate vessel, water (19.0 parts) was added to 13.6 parts of Aquatac 9027 (Sylvachem Corp.) tackifier self-emulsifiable hydrocarbon rosin) at 55-65 degrees C. with slow agitation. The resulting emulsion was 30 then heated and stirred for ten minutes at 60-65 degrees C.

Mixture A was then added to the emulsion and stirring was continued for one hour at a temperature of 60-65 degrees C. The resulting product was slowly cooled to room temperature, with stirring, while 24.4 parts of UCAR 174 latex emulsion (Union Carbide Corp.) were added at 55-60 degrees C. A solution of 0.44 parts of zinc acetate dihydrate cross-linking agent in 1.9 parts of water was then added with stirring at room temperature. Stirring was continued for ten more minutes to complete the formulation process.

Any preferred method of coating or application of the adhesive may be used, several such procedures having been described hereinabove.

The final "dried" film constitutes a heterogeneous system in which the aqueous zones or islands defined by the water receptive polymer extend through the thickness of the film and are distributed throughout the expanse of a continuous matrix consisting of the adhesive polymer in combination with the adhesive-augmenting tackifier. The described structure is illustrated schematically in the drawing of FIG. 1.

The detailed description of the preparation of a preferred embodiment of the conductive adhesive composition of the invention pertains to Example 1 in TABLE II. For the most part, the procedures for preparing the remaining formulations are either identical or quite similar, except for certain obvious modifications made to adapt the technique to differing materials. Such changes will be obvious to those skilled in the art and, accordingly, no detailed description of each such deviation is deemed essential.

While this invention has been described with reference to preferred embodiments and procedures, it is evident that the invention is not limited thereto. Further modifications of the method and products disclosed herein which fall within the scope of the following claims will be immediately evident to those skilled in the art. To the extent that these changes and modifications are within the scope of the appended claims, they are to be considered a part of this invention.

What is claimed is:

1. An electrically-conductive, pressure-sensitive, adhesive which may be applied to a supporting substrate using conventional coating techniques,
    said adhesive comprising a heterogeneous composition including,
    viscoelastic polymeric phase for providing adhesive and coadhesive properties to said adhesive, and
    an electrically conductive aqueous phase comprising,
    water-receptive polymer means for absorbing moisture and deterring surface wetness on said adhesive, and for enhancing resistance of said adhesive to adverse effects of high relative humidity,
    electrolyte means for imparting electrical conductivity to said adhesive, and
    humectant means for entraining and retaining moisture in said adhesive to ensure and to enhance the conductivity of said adhesive within a broad range of ambient relative humidity conditions, for acting in combination with said electrolyte means for preventing high electrical impedance in said adhesive,
    said viscoelastic polymeric phase and said aqueous phase being intimately interdispersed to provide a stable composition.

2. The adhesive as set forth in claim 1 wherein said adhesive constitutes a film having a through thickness in the range of from about 1.0 to about 10 mils.

3. The adhesive as set forth in claim 1 wherein said viscoelastic polymeric phase includes a synthetic latex.

4. The adhesive as set forth in claim 1 and further comprising tackifier means for augmenting the adhesive properties of said viscoelastic polymeric phase.

5. The adhesive as set forth in claim 1 wherein said water-receptive polymer means is sodium carboxymethylcellulose or cross-linked sodium carboxymethylcellulose.

6. The adhesive as set forth in claim 1 wherein said electrolyte means includes an alkali metal chloride, or ammonium chloride.

7. The adhesive as set forth in claim 1 wherein said humectant means includes a polyhydric alcohol.

8. The adhesive a set forth in claim 7 wherein said humectant means is glycerol.

9. The adhesive as set forth in claim 1 and further comprising polyvinyl alcohol as a film enhancer.

10. The adhesive as set forth in claim 1 and further comprising zinc acetate dihydrate.

11. A heterogeneous, pressure-sensitive, electrically conductive moisture equilibrating adhesive for biomedical electrodes,
    said adhesive comprising a permanently tacky, thin, viscoelastic polymeric adhesive phase and an electrically conductive aqueous phase containing a water-receptive polymer, a humectant and an electrolyte, said adhesive being derived from a formulation including the following components in the following parts by weight:

| | |
|---|---|
| Water | 30–60 |
| Latex emulsion | 5–35 |
| | (Polymer solids) |
| Humectant | 10–30 |
| Electrolyte | 1–10 |
| Water receptive polymer | 0.2–10 |

12. An electrically-conductive, pressure-sensitive, moisture-equilibrating adhesive comprising a permanently tacky, thin viscoelastic film constituting a high-strength interbonding coating on a supporting backing sheet of a disposable biomedical electrode for fastening the electrode to a substrate, said adhesive being derived from a formulation including, in combination, the following components in the following relative parts-by-weight ratio:

| | |
|---|---|
| Water | 30–60 |
| Latex emulsion | 5–35 |
| | (Polymer Solids) |
| Humectant | 10–30 |
| Tackifier | 5–25 |
| Electrolyte salt | 1–10 |
| Water receptive polymer | 0.2–10 |
| Film forming enhancer | 0.5–3 |
| Cross-linking agent | 0.2–1 |

13. An electrically-conductive, pressure-sensitive, moisture-equilibrating adhesive comprising a permanently tacky, thin viscoelastic film constituting a high-strength interbonding coating on a supporting backing sheet of a disposable bio-medical electrode for fastening the electrode to a substrate, said adhesive being derived from a formulation including, in combination, the following components in the following relative parts-by-weight ratio:

| | |
|---|---|
| Water | 39 |
| Acrylic latex (emulsion) | 24 |
| Glycerol | 18 |
| Tackifier | 13.5 |
| NaCl | 2 |
| Cross-linked carboxy methyl cellulose | 2 |
| Polyvinyl alcohol | 1 |
| Zinc acetate dihydrate | 0.5 |

14. A heterogeneous, pressure-sensitive, electrically conductive, moisture equilibrating adhesive for biomedical electrodes, said adhesive comprising a film-like matrix of an adhesive polymer derived from a latex emulsion, water-retentive zones constituting islands of a water-receptive polymer distributed throughout said matrix, said islands housing therewithin as solutes in water and intimately associated with said water-receptive polymer, electrolyte means for imparting electrical conductivity to said adhesive, and humectant means for entraining moisture in said adhesive for ensuring and enhancing conductivity capability of said adhesive within a broad range of ambient relative humidity conditions.

* * * * *